US005859268A

United States Patent [19]
Angelici et al.

[11] Patent Number: 5,859,268
[45] Date of Patent: Jan. 12, 1999

[54] PROCESS FOR THE SYNTHESIS OF α, β-UNSATURATED ESTERS

[75] Inventors: Robert J. Angelici, Ames, Iowa; Kuo-Chen Shih, Kaohsiung, Taiwan

[73] Assignee: Iowa State University Research Foundation, Inc., Ames, Iowa

[21] Appl. No.: 826,946

[22] Filed: Apr. 8, 1997

Related U.S. Application Data

[60] Provisional application No. 60/015,395 Apr. 9, 1996.
[51] Int. Cl.$^6$ .......................... C07C 51/347; C07C 69/74; C11C 1/00
[52] U.S. Cl. ............................. 554/126; 554/75; 560/205
[58] Field of Search ........................ 554/126, 75; 560/205

[56] References Cited

PUBLICATIONS

C. Adams et al., "Synthesis and $^1$H–, $^{13}$C–, and $^{57}$Fe–NMR Spectra of Mono– and Bis[tricarbonyl($\eta^4$–diene)iron], and ($\eta^3$–Allyl)tetracarbonyliron Trifluoroborate Complexes$^1$)", *Helvetica Chimica Acta*, 71, pp. 1116–1142 (1988).

S.J. Ainsworth, "Personal Care Products", *Chemical & Engineering News*, pp. 34–45 (17 Apr. 1995).

T. Akiyama et al., "Photolytic Cleavage and Isomerization Reactions of (1–σ,4–6–$\eta^3$–Organo)tricarbonyliron Complexes Involving an ($\eta^4$–Diene) ($\eta^{2-olefin)Fe(CO)_2}$ Intermediate. Quantum Yields and Mechanistic Studies.", *Organometallics*, 2, pp. 157–160 (1983).

J.A. Barve et al., "Fatty Acids, Part 33: The Synthesis of all the Octadecynoic Acids and all the Trans–Octadecenoic Acids", *Chem. Phys. Lipids*, 7, pp. 311–323 (1971).

F. Birencwaig et al., "Amminotetracarbonyl Iron (O) Complexes", *Tetrahedron Letters*, 31, pp. 2947–2950 (1979).

A.J. Bowles et al., "Mass Spectra of Some Acyclic α,β–Unsaturated Aldehydes, Ketones and Esters", *Organic Mass Spectrometry*, 2, pp. 809–818 (1969).

A.M. Brodie et al., "Some π–Hetero–1,3–diene Complexes of Iron Carbonyl", *Journal of the Chemical Society*, 18, pp. 2031–2035 (1972).

G. Cardaci et al., "Kinetics and Mechanism of Substitution of Olefinic Ligands by Carbon Monoxide in Tetracarbonyl–π–olefiniron Complexes", *Journal of the Chemical Society*, 19, pp. 2289–2293 (1972).

G. Cardaci, "Mechanism of Formation of (α,β) Unsaturated Aldehyde– and Ketone–Iron Tricarbonyl Complexes from the Corresponding Iron–Tetracarbonyl Complexes", *Journal of the American Chemical Society*, 97, pp. 1412–1415 (1975).

P.A. Chaloner, *Handbook of Coordination Caralysis in Organic Chemistry*, Butterworths; London, pp. 403–450 (1986).

F.A. Cotton et al., "Reactivity of Diiron Nonacarbonyl in Tetrahydrofuran. I. The Isolation and Characterization of Pyridinetetracarbonyliron and Pyrazinetetracarbonyliron", *Journal of the American Chemical Society*, 96, pp. 3438–3442 (1974).

R. Damico, "Iron Carbonyl Catalyzed Isomerization of Unsaturated Ethers and Esters. The Effect of Carbomethoxy and Methoxy Groups on Olefin Equilibria", *The Journal of Organic Chemistry*, 33, pp. 1550–1556 (1968).

J. Elzinga et al., "Intermediate Complex in the Reduction of Trimethylamine Oxide by Pentacarbonyl Iron: Its Use as Catalyst in the Addition of Carbon Tetrachloride to Carbon–Carbon Double Bonds", *J.C.S. Chem Comm.*, 20, pp. 705–706 (1977).

*Fatty Acids in Industry*, edited by R.W. Johnson et al., Marcel Dekker, New York, New York, 1989, Title Page and Table of Contents only.

H. Fleckner et al., "Tricarbonylbis($\eta^2$–cis–cyclooctene)iron: Photochemical Synthesis of a Versatile Fe(CO)$_3$ Source for Olefin Isomerization and Preparative Applications", *J. Am. Chem. Soc.*, 106, pp. 2027–2032 (1984).

M.B. France et al., "An Iridium–based Catalyst System for Metathesis/Isomerization of Acyclic Olefins, including Methyl Oleate", *J. Chem. Soc., Chem. Commun.*, pp. 1307–1308 (1994).

E.N. Frankel et al., "Catalytic Hydroformylation and Hydrocarboxylation of Unsaturated Fatty Compounds", *J. Am. Oil Chemists' Soc.*, 54, pp. 873–881 (1977).

E.N. Frankel et al., "Conjugation of Soybean Oil by Decomposition of Its Iron Tricarbonyl Complex with Carbon Monoxide", *J. Am. Oil Chemists' Soc.*, 44, pp. 37–39 (1967).

E.N. Frankel et al., "Isomerization of Unsaturated Fatty Esters by Iron Pentacarbonyl, Preparation of Iron Tricarbonyl Complexes of Polyunsaturated Fats", *J. Am. Oil Chemists' Soc.*, 43, pp. 307–311 (1966).

D.J. Frost et al., "The PMR Analysis of Non–Conjugated Alkenoic and Alkynoic Acids and Esters", *Chemistry and Physics of Lipids*, 15, pp. 53–85 (1975).

W. Gerhartz et al., "Low–Temperature Photochemistry of Matrix–Isolated Fe(CO)$_4$ Complexes of α,β–Unsaturated Esters: C=C vs. Ester Group Coordination", *Organometallics*, 6, pp. 1850–1856 (1987).

F.–W. Grevels et al., "Photochemical Synthesis of Bis($\eta$–methyl acrylate)tricarbonyliron", *Angew. Chem. internat. Edit.*, 13, pp. 534–536 (1974).

W.P. Griffith et al., "Vibrational Spectra of Metal–Metal Bonded Complexes of Group VIII", *J. Chem. Soc. (A)*, 5, pp. 834–839 (1969).

G. Grimmer et al., "Synthese von cis–Formen α,β–Ungesättigter Carbonsäuren", *Liebigs Annalen Der Chemie*, 685, pp. 154–160 (1965).

J. Hine et al., "Double Bond Stabilizing Abilities of Formyl, Carbo–tert–butoxy, and Carbomethoxy Substituents", *J. Org. Chem.*, 47, pp. 2745–2748 (1982).

J. Hine et al., "Electronic Effects of Substituents on the Stabilities of Carbon–Carbon Double Bonds", *Journal of the American Chemical Society*, 95, pp. 1179–1185 (1973).

(List continued on next page.)

Primary Examiner—Paul J. Killos
Attorney, Agent, or Firm—Mueting, Raasch & Gebhardt, P.A.

[57] ABSTRACT

The present invention provides a process for the synthesis of an α,β–unsaturated ester from a mono-olefin-ester using Fe(CO)$_5$.

22 Claims, 1 Drawing Sheet

PUBLICATIONS

D.R. Howton, "Preparation of trans–2–Octadecenoic Acid", *Organic Preparations and Procedures Int.,* 6, pp. 175–178 (1974).

A.J. Hubert et al., "The Isomerization of Olefins Part I. Base–Catalysed Isomerization of Olefins", *International Journal of Methods in Synthetic Organic Chemistry,* 3, pp. 97–112 (1969).

A.J. Hubert et al., "The Isomerization of Olefins Part II. Thermal and Catalytic Isomerization of Olefins using Acids, Metals, Metal Complexes, or Boron Compounds as Catalysts", *International Journal of Methods in Synthetic Organic Chemistry,* 8 pp. 405–430 (Aug. 1970).

M. Khan et al., "Allylic Oxidation of Methyl trans–2–Octadecenoate by Chromium Trioxide", *Indian Journal of Chemistry,* 25B, pp. 321–323 (1986).

Kerber, *Comprehensive Organometallic Chemistry,* Abel et al., Pergamon Press, 7, (1995), Title Page and Table of Contents only.

J.S. Kristoff et al., "Adduct Formation and Carbonyl Rearrangement of Polynuclear Carbonyls in the Presence of Group III Halides", *Inorganic Chemistry,* 13, pp. 499–506 (1974).

P.J. Kropp et al., "Photochemistry of Cycloalkenes. IV. Comparison with Crotonic Acid", *The Journal of Organic Chemistry,* 32, pp. 3222–3223 (1967).

T. Kruck et al., "Über das Reaktionsverhalten von Pentakis(trifluorophosphin)–eisen(0) gegenüber aktivierten Monoolefinen", *Chemische Berichte,* 106, pp. 3578–3587 (1973).

W. Lauwers et al., "Studies in Organic Mass Spectrometry—XIII: Investigation of Electron–Impact–Induced Isomerisation of $\alpha,\beta-$ and $\beta,\gamma$–Unsaturated Esters", *Organic Mass Spectrometry an Internat'l Journal,* 7, pp. 1027–1037 (1973).

C.F. Lochow et al., "Nickel–Promoted Isomerizations of Alkenes Bearing Polar Functional Groups", *J. Org. Chem.,* 41, pp. 3020–3022 (1976).

T.A. Manuel, "Some Reactions of Monoölefins with Iron Carbonyls", *J. Org. Chem.,* 27, pp. 3941–3944 (1962).

D.E. McGreer et al., "Pyrazolines. Part II", *Can. J. Chem.,* 38, pp. 2410–2416 (1960).

D.E. McGreer et al., "Thermal rearrangement of $\alpha,\beta-$ to $\beta,\gamma$–unsaturated esters. Evidence for a 1,5–hydrogen transfer mechanism", *Can. J. Chem.,* 46, pp. 2225–2232 (1968).

R.J. McKinney, "Kinetic Control in Catalytic Olefin Isomerization. An Explanation for the Apparent Contrathermodynamic Isomerization of 3–Pentenenitrile", *Organometallics,* 4, pp. 1142–1143 (1985).

Miginiac et al., "Action D'Organozinciques $\alpha$–Ethyleniques sur le Chloroformiate D'Ethyle: Preparation D'Esters $\beta$–Ethyleniques", *Journal of Organometallic Chemistry,* 96, pp. 163–168 (1975).

Norman, *Inorganic Reactions and Methods,* 16, VCH Publishers; New York, New York 1993, Title Page and Table of Contents only.

B. Palameta et al., "Erythro and Threo–1,2,3–Octadecanetriols", *Tetrahedron,* 19, pp. 1463–1470 (1963).

A.J. Pearson, "Iron Compounds in Organic Synthesis", Academic Press, San Diego, CA, 1994, Title page and Table of Contents only.

S. Rafat Husain et al., "Synthesis of Sulfur–Containing Derivatives from Olefinic Fatty Esters", *JAOCS,* 60, pp. 1340–1344 (1983).

R.G. Salomon, "Tetrahedron Report No. 143", *Tetrahedron,* 39, pp. 485–575 (1983).

M.A. Schroeder et al., "Pentacarbonyliron(0) Photocatalyzed Hydrogenation and Isomerization of Olefins", *J. Am. Chem. Soc.,* 98, pp. 551–558 (1976).

E.H. Schubert et al., "The Photochemical Synthesis of Pentacarbonyliron(0) Derivatives", *Inorganic Chemistry,* 5, pp. 1071–1074 (1966).

J.–K. Shen et al., "Kinetic studies of CO substitution of metal carbonyls in the presence of O–atom transfer reagents", *Coordination Chemistry Review,* 128, pp. 69–88 (1993).

K.–C. Shih et al., "Iron Carbonyl–Promoted Isomerization of Olefin Esters to Their $\alpha,\beta$–Unsaturated Esters: Methyl Oleate and Other Examples", *The Journal of Organic Chemistry,* 61, pp. 7784–7792 (1996).

H. Singer et al., "Isomerisierungen Olefiniseher Carbonsäureester mit rhodiumkomplexen", *Tetrahedron,* 28, pp. 5769–5777 (1972).

H.K. van Dijk et al., "Low temperature photochemistry of [$Fe_2(CO)_6$(bipy)–(P(n–Bu)$_3$)]. Stabilization of an intermediate photoproduct in a decomposition reaction" *Journal of Organometallic Chemistry,* 340, pp. 227–238 (1988).

von Gustorf et al., "Tri– und Tetracarbonyleisen–Komplexe der Isobutyliden–meldrumsäure", *Zeitschrift für Naturforschung,* 27B, pp. 575–576 (1972).

PROCESS FOR THE SYNTHESIS OF α, β-UNSATURATED ESTERS

This application claims priority from a provisional patent application filed on Apr. 9, 1996 entitled "Process for the Synthesis of the Alpha,Beta-Isomer of Methyl Oleate" and assigned Provisional Serial No. 60/015,395, which is incorporated herein by reference.

BACKGROUND OF THE INVENTION

The isomerization of olefins is catalyzed by a variety of agents including bases, acids, and a plethora of transition metal complexes. These catalysts yield a thermodynamic mixture of isomeric olefins if the isomerizations are allowed to proceed to equilibrium. Non-thermodynamic distributions of products are obtained if equilibrium is not achieved, but it is rare that olefin isomerization leads to high yields of one isomer unless it is highly favored thermodynamically.

As there is considerable commercial interest in transformations of olefin-esters to their α,β-unsaturated esters, particularly the transformation of esters of oleic acid, it would be highly desirable to perform the isomerization in Equation 1.

This is a particularly challenging isomerization because of the many olefin isomers that are possible within the seventeen-carbon hydrocarbon chain. Because none of these isomers is highly favored thermodynamically, the α,β-unsaturated ester isomer has been prepared by very elaborate methods. See, for example, Howton, *Org. Prep. Proc. Int.*, 6, 175, 1974; Barve et al., *Chem. Phys. Lipids*, 7, 311, 1971, Grimmer et al., *Lieb. Annt. Chem.*, 685, 154, 1965; and Palameta et al., *Tetrahedron*, 19, 1463, 1963. A less complex method for such syntheses would be highly desirable. A less complex method that would promote the isomerization in Equation 1 could presumably also be used for the isomerization of other mono-ene esters to α,β-unsaturated esters. Such reactive products would be useful intermediates for the synthesis of other new compounds.

Iron carbonyls have been used extensively as catalysts for the isomerization of olefins. For example, 1-pentene isomerizes to give an equilibrium mixture of cis-2-pentene (21%) and trans-2-pentene (76%) in the presence of $Fe(CO)_5$ in $C_6H_6$ solvent under ultraviolet photolysis (Schroeder et al., *J. Am. Chem. Soc.*, 98, 551, 1976). The same product distribution is obtained when $Fe(CO)_3(cis\text{-}cyclooctene)_2$ catalyzes 1-pentene isomerization without photolysis (Fleckner et al., *J. Am. Chem. Soc.*, 106, 2027, 1984). A mixture of isomers is obtained from the $Fe_3(CO)_{12}$-catalyzed isomerizations of n-hexenes, n-pentenes, and methyl-1-pentenes under reflux (Manuel et al., *J. Org. Chem.*, 27, 3941, 1962). Similarly, $Fe(CO)_5$ catalyzes the isomerization of n-alkenyl- and cyclohexenylcarboxylate esters and ethers to a mixture of isomers when refluxed (125°–150° C.) in hydrocarbon solvents or photolyzed at 20° C. (Damico, *J. Org. Chem.*, 33, 1550, 1968). Methyl oleate itself has been reported to give a very complex mixture of olefin isomers when heated at 185° C. with $Fe(CO)_5$; however, in this mixture the amount of the α,β-ester isomer was too small to be detected (Frankel et al., *J. Am. Oil Chem. Soc.*, 43, 307, 1966).

Not only do the iron carbonyls catalyze olefin isomerization but there is evidence that under the proper conditions they might weakly stabilize the α,β-ester isomer (Equation 1) by coordinating it as an $\eta^4$-oxadiene to $Fe(CO)_3$ as in A.

Isolable $Fe(CO)_3$ complexes of $\eta^4$ α,β-unsaturated aldehydes (RCH=CH—C(=O)H), ketones (RCH=CH—C(=O)R') and imines (RCH=CH—C(=NR')H) are well known. The olefin-esters, $\eta^4$ methyl acrylate and methyl trans-crotonate, also form $\eta^4$ complexes, $Fe(CO)_3(\eta^4\text{-}H_2C=CHCO_2Me)$ and $Fe(CO)_3$ ($\eta^4\text{-}CH_3CH=CHCO_2Me$), that have been detected in ultraviolet-irradiated, low temperature matrices (10–12 K) containing $Fe(CO)_5$ and the α,β-unsaturated esters. Even at −5° C., $Fe(CO)_3$ ($\eta^4\text{-}H_2C=CHCO_2Me$) has been observed in n-hexane where it is in equilibrium with $Fe(CO)_3(\eta^2\text{-}H_2C=CHCO_2Me)_2$, whose concentration depends on the concentrations of the complex and added methyl acrylate.

Although such studies suggest that it may be possible to stabilize the α,β-ester isomer of methyl oleate by $\eta^4$ coordination to $Fe(CO)_3$ if the complex (of type A) is produced at relatively low temperatures, this would mean that $Fe(CO)_5$ must catalyze the isomerization at low temperature. However, $Fe(CO)_5$ is known to be inactive as an olefin isomerization catalyst at low temperatures (e.g., at temperatures below about 0° C. Furthermore, although at high temperatures (e.g., at temperatures greater than about 125° C.), $Fe(CO)_5$ is an olefin isomerization catalyst, the α,β-ester isomer cannot be stabilized by η4 coordination to $Fe(CO)_3$ because the complex of type A is not stable at such high temperatures.

SUMMARY OF THE INVENTION

The present invention provides processes for the synthesis of an α,β-unsaturated ester from a mono-olefin-ester using $Fe(CO)_5$. In one embodiment, the process includes the steps of: exposing a mixture of a mono-olefin-ester and $Fe(CO)_5$ to ultraviolet radiation; and adding a coordinating ligand or oxidizing agent to the mixture under conditions effective to produce an α,β-unsaturated ester. In another embodiment, the process includes the steps of: combining a mono-olefin-ester and $Fe(CO)_5$ under conditions effective to form $Fe(CO)_3(\eta^4\text{-}\alpha,\beta\text{-ester})$; and adding a displacing reagent (e.g., a coordinating ligand or oxidizing agent such as $O_2$) to the $Fe(CO)_3(\eta^4\text{-}\alpha,\beta\text{-ester})$ to displace the α,β-ester ligand and form free α,β-unsaturated ester. In yet another embodiment, the process includes the steps of: exposing $Fe(CO)_5$ to ultraviolet radiation in the presence of a weakly coordinating ligand to form $Fe(CO)_3L_x$, wherein L represents the weakly coordinating ligand and x=1 or 2; adding a mono-olefin-ester to the $Fe(CO)_3L_x$ to form $Fe(CO)_3(\eta^4\text{-}\alpha,\beta\text{-ester})$; and adding a displacing reagent to the $Fe(CO)_3(\eta^4\text{-}\alpha,\beta\text{-ester})$ to displace the α,β-ester ligand and form free α,β-unsaturated ester.

The present invention also provides a process for the synthesis of an ester from a mono-olefin-ester. The process includes the steps of: combining a mono-olefin-ester and Fe(CO)$_5$ under conditions effective to form Fe(CO)$_3$($\eta^4$-α,β-ester); and treating Fe(CO)$_3$($\eta^4$-α,β-ester) with an electrophile to form an ester. The electrophile is preferably an acid of the form HX, wherein X is F, Cl, Br, I, CH$_3$CO$_2$, RSO$_3$, R$_3$PO$_4$, and the like.

DETAILED DESCRIPTION OF THE INVENTION

As noted above, the isomerizatin of olefins is catalyzed by numerous transition metal complexes as well as strong acids and bases. However, these isomerizations normally result in the formation of a mixture of olefin isomers because they all have similar thermodynamic stabilities. The process of the present invention preferably solves this problem by using ultraviolet radiation to photolyze a mixture of Fe(CO)$_5$ and mono-olefin-esters (i.e., molecules in which the C=C bond is not in conjugation with the C=O bond). Alternatively, the Fe(CO)$_5$ can be initially exposed to ultraviolet radiation when in the presence of a weakly coordinating ligand (e.g., cis-cyclooctene) that is effective at stabilizing the Fe(CO)$_{5-x}$ moiety (x=1 or 2) until the mono-olefin-ester is added to the mixture, although this is not the preferred way to carry out the photolysis step. Once the photolysis step has been carried out, it is followed by a step of treating the reaction mixture with a coordinating ligand to give the free (i.e., uncoordinated) α,β-ester.

The process of the present invention (e.g., the photolysis step and the treatment step) is carried out for a time and at a temperature effective to produce the corresponding free α,β-unsaturated ester (also referred to herein as the α,β-ester). Preferably, the process of the present invention is carried out under conditions that produce the free (i.e., uncoordinated) α,β-ester in an amount of at least about 25% yield, more preferably, at least about 40% yield, and most preferably, in at least about 70% yield, with yields as high as 90% often being possible.

The mono-olefin-ester is one in which the C=C bond is not in conjugation with the C=O bond. It is of the general formula (R$^1$)(R$^2$)C=C(R$^3$)—R$^4$—CO$_2$R$^5$. The R groups can be a wide variety of organic groups (or H for R$^1$, R$^2$, and R$^3$) optionally including functional groups that are not capable of coordinating with the iron center. That is, the functional groups can be any that do not contain coordinating atoms such as O, S, N, P, Sb, and As. Such mono-olefin-esters include a variety of vegetable oils, such as soybean, corn, etc., and animal fats. Partially hydrogenated vegetable oils can also be converted to α,β-esters. For example, the fatty acid groups in soybean oil are 53% linoleic acid, which contains an ester group and two olefin groups. Upon partial hydrogenation, linoleic acid can be converted to a molecule with an ester group and one olefin group, which can then be used in the process of the present invention.

Preferably, in the formula (R$^1$)(R$^2$)C=C(R$^3$)—R$^4$—CO$_2$R$^5$, each R$^1$, R$^2$, and R$^3$ is independently H or an alkyl group, R$^4$ is a divalent alkylene group that does not contain any quaternary carbon atoms, and R$^5$ is an alkyl group. The alkyl groups can include functional groups. R$^4$ may have functional groups in the side chains but not in the main chain, and may have aromatic groups in the side chains but not in the main chain (i.e., in the chain between the C=C and the ester group). As stated above, the functional groups can be any that are not capable of coordinating with the iron center. That is, the functional groups can be any that do not contain coordinating atoms such as O, S, N, P, Sb, and As.

It is believed that the process involves the isomerization of the mono-olefin ester to a conjugated α,β-ester with formation of the intermediate Fe(CO)$_3$($\eta^4$-α,β-ester). In this intermediate complex, the α,β-unsaturated ester isomer of the mono-olefin ester is stabilized by $\eta^4$-oxadiene π coordination of the olefin and ester carbonyl groups to the Fe(CO)$_3$ unit. This was unexpected in that a variety of other products were expected to have been formed (e.g., the $\eta^2$ product). Although it is not intended to be limiting to the claimed invention, it is believed that, upon photolysis, there is initial dissociation of one CO group and coordination of the olefin group of the olefin-ester to the Fe(CO)$_4$ unit. Additional photolysis is believed to remove another CO ligand which allows the double bond to migrate to the α,β-position and the ester carbonyl group to bind to the metal to give the Fe(CO)$_3$($\eta^4$-α,β-ester) complex. Alternatively, if the photolysis can be carried out initially in the presence of a weakly coordinating ligand, it is believed that Fe(CO)$_3$L$_x$ is formed, wherein L represents the weakly coordinating ligand and x=1 or 2. Subsequently, the mono-olefin-ester is added to the Fe(CO)$_3$L$_x$ to displace the weakly coordinating ligand(s) and form Fe(CO)$_3$($\eta^4$-α,β-ester). Such weakly coordinating ligands are effective at stabilizing the Fe(CO)$_{5-x}$ moiety (x=1 or 2) until the mono-olefin ester is added to the mixture. These include, for example, cis-cyclooctene, other alkenes, ethers (R$_2$O), alkyl or aryl halides, and esters.

Once the mono-olefin-ester has been reacted with the photolyzed Fe (CO)$_5$, presumably forming a Fe (CO)$_3$($\eta^4$-α,β-ester) complex, the reaction mixture is treated with a ligand that is more strongly coordinating than the $\eta^4$-oxadiene π ligand, e.g., pyridine or CO, to displace the α,β-ester ligand and form free (i.e., uncoordinated) α,β-unsaturated ester. Alternatively, the intermediate Fe(CO)$_3$ ($\eta^4$-α,β-ester) complex could be treated with another type of displacing reagent, such as an oxidizing agent (e.g., O$_2$ or cerium(IV) ammonium nitrate), to displace the α,β-ester ligand, or an electrophile capable of adding to the olefin bond and forming an ester. Such electrophiles include, for example, acids of the form HX, wherein X is F, Cl, Br, I, CH$_3$CO$_2$, RSO$_3$, R$_3$PO$_4$, and the like.

The optimum time for the photolytic reaction depends, for example, upon the intensity of the UV source and the arrangement of the source and the reaction mixture, and the temperature of the reaction mixture. Preferably, the photolysis step of the process is carried out for at least about 10 minutes, more preferably, for at least about 1 hour, even more preferably, for at least about 2 hours, and most preferably, for at least about 3 hours. Typically, the shorter the photolysis time, the lower the yield (see Table 2, below). This is believed to be due to incomplete reaction between Fe(CO)$_5$ and the olefin-ester. Preferably, the photolysis step of the process is carried out for no greater than about 24 hours, more preferably, for no greater than about 6 hours, even more preferably, for no greater than about 4 hours, and most preferably, for no greater than about 3 hours. Typically, the longer the photolysis time, the higher the yield (see Table 2, below), although photolysis times that are too long can result in lower yields. Although it is not intended to be limiting, this is believed to be due to decomposition of the intermediate Fe(CO)$_3$($\eta^4$-$\alpha,\beta$-ester) and isomerization of the $\alpha,\beta$-ester to a mixture of olefin-ester isomers.

The temperature of the reaction mixture during the photolysis step is within a range effective to produce an $\alpha,\beta$-ester. It is believed that this is a temperature that is effective to stabilize the intermediate $\eta^4$-oxadiene $\pi$ complex. Preferably, this reaction is carried out at a temperature of no greater than about 50° C., more preferably, at a temperature of no greater than about 20° C., even more preferably, at a temperature of no greater than about 10° C., and most preferably, at a temperature of no greater than about 0° C. Typically, the higher the temperature of the reaction mixture during photolysis, the lower the yield (see Table 2, below). Although it is not intended to be limiting, this is believed to be due to decomposition of the intermediate Fe(CO)$_3$ ($\eta^4$-$\alpha,\beta$-ester) and isomerization of the $\alpha,\beta$-ester to a mixture of olefin-ester isomers. Preferably, the temperature of the reaction mixture during the photolysis step of the process is no less than about −80° C., although it does not appear that yields are decreased with even lower temperatures.

Another consideration in the process of the present invention is the concentration of the Fe(CO)$_5$ and mono-olefin-ester reactants. The Fe(CO)$_5$ and mono-olefin-ester are typically used in approximately stoichiometric (i.e., equimolar) amounts (i.e., ±10%), however, one of the reactants can be used in excess. Preferably, the concentration of each is initially present in the reaction mixture in no greater than about 500 mM, more preferably, no greater than about 50 mM, and most preferably, no greater than about 15 mM. If the concentrations are too high, photolysis of Fe(CO)$_5$ can produce insoluble Fe$_2$(CO)$_9$, which can produce low yields of the $\alpha,\beta$-ester.

The photolysis step of the process of the present invention can be carried out with a neat reaction mixture (i.e., in which the Fe(CO)$_5$ acts as the solvent), although preferably, the reaction mixture includes an organic solvent. The organic solvent is preferably a noncoordinating solvent (i.e., one that is not coordinating to the iron center), such as a hydrocarbon solvent, a perfluorocarbon solvent. Examples of suitable hydrocarbon solvents include hexanes, toluene, as well as other alkanes and arenes. More preferably, the solvent is an alkane, such as pentane, heptane, hexanes, and the like. Typically, a coordinating solvent, such as THF, is believed to be undesirable because it may compete with the mono-olefin-ester for coordination to the iron with the result that the $\alpha,\beta$-ester is produced in low yield.

Subsequent to photolysis, the reaction mixture is treated with a coordinating ligand (i.e., a ligand capable of coordinating to the iron center) or other type of displacing reagent. Because it is believed that the intermediate product is Fe(CO)$_3$($\eta^4$-$\alpha,\beta$-ester), this coordinating ligand is one that is more strongly coordinating to the iron center than the $\alpha,\beta$-ester. That is, it is a ligand that is capable of displacing the $\alpha,\beta$-ester from the iron center. Examples of such coordinating ligands include pyridine, CO, PMe$_3$ and other phosphines, as well as arsines, amines, sulfides (R$_2$S), diene olefins, and the like. Typically, a large excess (e.g., 20-fold excess) of this coordinating ligand is used. It is added to the reaction mixture under conditions effective to produce the free (i.e., uncoordinated) $\alpha,\beta$-ester. The preferred coordinating ligand is CO because it reforms Fe(CO)$_5$, which can be reused in the process. The other complexes Fe(CO)$_5$(py)$_2$ or Fe(CO)$_3$(PMe$_3$)$_2$, for example, are expensive and not easily recycled. Alternatively, O$_2$ or other oxidizing agents, such as cerium(IV) ammonium nitrate, can be used in place of a coordinating ligand, which would likely oxidize the complex to Fe$_2$O$_3$. This iron oxide could be separated from the desired product by filtration, however, it would not allow for easy recycling of the iron to Fe(CO)$_5$.

The optimum time for this step (e.g., displacement step) of the process depends, for example, upon the nature and amount of the coordinating ligand or oxidizing agent, and the temperature of the reaction mixture. Preferably, this step of the process is carried out for at least about 0.5 minute, more preferably, for at least about 1 minute, even more preferably, for at least about 5 minutes, and most preferably, for at least about 10 minutes. Preferably, this step of the process is carried out for no greater than about 1 hour, more preferably, for no greater than about 30 minutes, even more preferably, for no greater than about 20 minutes, and most preferably, for no greater than about 10 minutes.

The temperature of the reaction mixture during this step (e.g., displacement step) of the process is within a range effective to produce free $\alpha,\beta$-ester. Preferably, this reaction is carried out at a temperature of no greater than about 50° C., more preferably, at a temperature of no greater than about 30° C., even more preferably, at a temperature of no greater than about 20° C., and most preferably, at a temperature of no greater than about 0° C. Preferably, the temperature of the reaction mixture during this step of the process is no less than about −40° C., more preferably, no less than about −30° C., even more preferably, no less than about −20° C., and most preferably, no less than about 0° C.

In order to prevent isomerization of the $\alpha,\beta$-ester during decomposition of Fe(CO)$_3$($\eta^4$-$\alpha,\beta$-ester) at temperatures above 0° C., CO or another coordinating ligand or oxidizing agent, for example, is preferably added to the reaction mixture at an initial temperature of about 0° C. or below. It is believed that this treatment results in displacement of the coordinated ester group from the metal to give Fe(CO)$_4$($\eta^2$-$\alpha,\beta$-ester). In order to completely displace the $\alpha,\beta$-ester, this complex is preferably heated in the presence of the displacing reagent (e.g., coordinating ligand or oxidizing agent) at elevated temperatures for an extended period of time (e.g., 50° C. for 12 hours). If the $\alpha,\beta$-ester ligand is displaced by CO, Fe(CO)$_5$ can be reformed. The Fe(CO)$_5$ can then be separated from the $\alpha,\beta$-ester product by distillation. Furthermore, the free $\alpha,\beta$-unsaturated ester can be purified by recrystallization. Alternatively, the $\alpha,\beta$-unsaturated ester can be used in the mixture of other isomers produced in the reaction (i.e., isomers resulting from migration of the C=C bond to sites other than the $\alpha,\beta$- position).

The process of the present invention was applied to the isomerization of methyl 3-butenoate to give methyl crotonate in 94% yield. This isomerization is favored thermodynamically at 250° C.: methyl traus-crotonate (83%), methyl cis-crotonate (12%), and methyl 3-butenoate (5%). At 0° C., the equilibrium amount of methyl trans-crotonate is likely to be even greater. In the Fe(CO)$_5$-promoted reaction, stabilization of traits-methyl crotonate as the Fe(CO)$_3$($\eta^4$-$\alpha,\beta$-ester) complex is not necessary for the formation of this product.

On the other hand, the isomerization of ethyl 4-methyl-4-pentenoate to ethyl tratis-4-methyl-2-pentenoate is not favored thermodynamically. In fact the equilibrium distribution of isomers at 25° C. is as follows: ethyl 4-methyl-3-pentenoate (90%) and ethyl 4-methyl-2-pentenoate (10%). Despite this adverse equilibrium, ethyl 4- methyl-trans-2-pentenoate is obtained in 90% yield using the process of the present invention. The isomerization of ethyl 4-methyl-4-pentenoate also shows that this method accommodates the isomerization of olefin-esters that contain a tertiary carbon.

Finally, the $Fe(CO)_5$-promoted isomerization of methyl oleate to its $\alpha,\beta$-isomer occurs in 70% yield. This yield is far greater than that expected thermodynamically. Using $RhCl(PPh_3)_3/SnCl_2$ to catalyze the isomerization of methyl oleate at 115° C. in chlorobenzene solvent, the equilibrium amount of the $\alpha,\beta$-ester isomer is only about 3.5%.

The process of the present invention is advantageous because the starting materials and reagents used are generally relatively inexpensive. For example, methyl oleate can be obtained from vegetable oils and animal fats, as well as from trees, and is a relatively inexpensive starting material. $Fe(CO)_5$ is also a relatively inexpensive liquid.

Because of the relatively high cost of producing $\alpha,\beta$-esters using conventional procedures, their uses have been limited. However, with the process of the present invention, it is anticipated that many applications will be found, some of which will be similar to the uses of methyl oleate. Methyl oleate and its derivatives are used widely as surfactants in soaps, industrial and household laundry products, and food emulsifiers. They are also used in oil-field chemicals, metal-working chemicals, cosmetics, and textiles. Other applications for the $\alpha,\beta$-esters produced by the process of the present invention include those in which fatty acids are used, such as in personal care products (e.g., shampoos, skin creams, etc.).

The invention will be further described by reference to the following detailed example. This example is offered to further illustrate the various specific and illustrative embodiments and techniques. It should be understood, however, that many variations and modifications may be made while remaining within the scope of the present invention.

EXPERIMENTAL SECTION

All reactions were performed under a nitrogen atmosphere in reagent grade solvents using standard Schlenk techniques. Hexanes and toluene were distilled under $N_2$ from $CaH_2$; tetrahydrofuran (THF) was distilled from Nat-benzophenone. Silica gel (Davisil 62; 150 mesh, 58Å) was purchased from Davison Chemical, Baltimore, Md. $Fe(CO)_5$ was purchased from Aldrich Chemical Co., Milwaukee, Wis, and used immediately after purification by bulb-to-bulb distillation. Methyl oleate (99%), methyl palmitate (99%), ethyl 4-methyl-4-pentenoate (98%), methyl trans-crotonate (98%), methyl 3-butenoate (97%), pyridine, cis-cyclooctene (99%), and $Fe_2(CO)_9$ (98%) were purchased from Aldrich and used without further purification.

The photochemical reactions were performed in a quartz tube equipped with a nitrogen bubbler using a 450 W mercury UV lamp. The temperatures (−35° C. to 20° C.) of the photochemical reaction solutions were maintained by a Lauda RK 20 constant temperature circulator. Infrared spectra were obtained on a Nicolet 710 FTIR spectrophotometer using a solution cell with NaCl salt plates (0.2 mm). Gas chromatographic analyses were performed with a temperature-programmed Varian 3400 GC using a 25 m HP-1 (cross-linked methylsilicone gum phase) capillary column (OV-101) with a flame ionization detector. A Varian 3400 GC interfaced to a Finnigan TSG 700 high resolution magnetic sector mass spectrometer with electron ionization (70 eV) was used for all GC-MS measurements. For analyses of methyl oleate and its isomers, the GC column temperature was held at 120° C. for 1 minute, followed by a 50° C./minute ramp to 200° C. After a 1 minute hold, a final ramp (2° C./minute) to 220° C. was used. For analyses of ethyl 4-methyl-4-pentenoate and its isomers, the column temperature was held at 50° C. for 5 minutes, followed by a 20° C./minute ramp to 150° C. The $^1H$ NMR spectra were recorded on a Nicolet NT-300 spectrometer using a deuteriated solvent as the internal lock and internal reference ($CDCl_3$: δ 7.25 ppm; $C_6D_6$: δ 7.16 ppm for $^1H$).

Irradiation (UV) of $Fe(CO)_5$ and Methyl trans-Crotonate. A solution of methyl trans-crotonate (28 μL, 0.27 mmol) and $Fe(CO)_5$ (35 μL, 0.27 mmol) in hexanes (20 mL) was allowed to come to temperature equilibrium at 0° C. for 30 minutes. Irradiation (UV) of the slightly yellow solution with a continuous nitrogen flow over the surface of the solution to remove the evolved CO gave a red solution. Approximately every 30 minutes, about 0.2 mL of the solution was removed by syringe for immediate FTIR analysis.

Irradiation of $Fe(CO)_5$ and Methyl 3-Butenoate. The same procedures were used for this reaction as for methyl trans-crotonate. After 6 hours of irradiation, the solution was treated with CO first at 0° C. for 1 hour and then at 50° C. for 12 hours as described in detail below in order to liberate the free methyl crotonate; the resulting product mixture (with a capillary containing reference $C_6D_6$) was identified by its $^1H$ NMR spectrum as being 94% methyl trans-crotonate and 6% of the starting methyl 3-butenoate. Their $^1H$ NMR spectra are as follows: methyl trans-crotonate (δ 7.47, d of q, J=15.6 and 6.9 Hz, olefin H at C3; 6.35, d of q, J=15.6 and 1.7 Hz, olefin H at C2; 4.19, s, $OCH_3$) and 6% of the starting methyl 3-butenoate (δ 5.65, d of apparent q, J=10.2, 1.5 and 1.5 Hz, olefin H at C4; 5.66, d of apparent q, J=17.1, 1.5 and 1.5 Hz, olefin H at C4; 6.51, d of d of t, J=16.8, 10.2 and 6.9 Hz, olefin H at C3; 3.57, d of t, J=6.9 and 1.5 Hz, H at C2; 4.17, s, $OCH_3$). Although not observed in this reaction, the $^1H$ NMR spectrum of methyl cis-crotonate in $C_6D_6$ is as follows: δ 7.47 (d of q, J=15.6 and 6.9 Hz, olefin H at C3), 6.35 (d of q, J=15.6 and 1.7 Hz, olefin H at C2), 4.19 (s, $OCH_3$).

Irradiation of $Fe(CO)_5$ and Methyl Oleate. A solution of methyl oleate (90 μL, 0.27 mmol) and $Fe(CO)_5$ (35 μL, 0.27 mmol) in hexanes (20 mL) at 0° C. was irradiated under a continuous nitrogen flow. The solution turned from pale yellow to red during the irradiation. As the irradiation was prolonged, the color of the solution turned to deep red. Periodically 0.5 mL of the solution was removed by syringe for analysis. A portion of the solution (0.2 mL) was syringed into the NaCl IR cell for immediate FTIR analysis. The other portion of the solution (0.3 mL) was added to a vial (1.5 mL) containing a 20-fold amount of pyridine; this solution was stirred at room temperature for 10 minutes and then analyzed by GC for the organic compounds. Similar procedures were used in irradiation experiments with different concentrations of $Fe(CO)_5$ and methyl oleate in different solvents (toluene and THF) and at a higher reaction temperature (20° C.).

Irradiation of $Fe(CO)_5$ and Ethyl 4-Methyl-4-pentenoate. This reaction was performed as described for methyl oleate.

Reaction of CO with an Irradiated Solution of $Fe(CO)_5$ and Methyl Oleate. A hexanes solution (20 mL) of $Fe(CO)_5$ (0.27 mmol) and methyl oleate (0.27 mmol) was irradiated at 0 ° C. for 3 h under a continuous $N_2$ flow to give $Fe(CO)_3$ ($\eta^4$-CH$_3$(CH$_2$)$_{14}$CH=CHCO$_2$Me). Then CO was bubbled through the solution at 0° C. for 1 hour, followed by stirring under the CO atmosphere at 50° C. for 12 hours. The resulting Fe(CO)$_5$ and solvent were vacuum distilled (bulb-to-bulb) from the reaction mixture. The residue was then chromatographed in hexanes through a short (1×10 cm) column (silica gel) to remove the iron impurities. The composition of the resulting solution was analyzed by GC as described above. The compounds present in the mixture were identified by the following $^1$H NMR spectra in CDCl$_3$, which are very similar to those reported in the literature (McGreer et al., *Can. J. Chem.*, 46, 2225, 1968; and Miginiac et al., *J. Organoiomet. Chem.*, 96, 163, 1975): methyl octadec-trans-2-enoate: δ 2.18 (apparent q of d, J=7.2, 7.2 and 1.5 Hz, H at C4), 6.96 (d of t, J=15.5 and 7.2 Hz, olefin H at C3), 5.81 (d of t, J=15.5 and 1.5 Hz, olefin H at C2), 3.71 (s, OCH$_3$); methyl octadec-cis-2-enoate: δ 2.63 (apparent q of d, J=7.5, 7.5 and 1.5 Hz, H at C4), 6.22 (d of t, J=11.4 and 7.5 Hz, olefin H at C3), 5.70 (d of t, J=11.4 and 1.5 Hz, olefin H at C2), 3.69 (s, CH$_3$); methyl octadec-trans-3-enoate: δ 2.02 (m, H at C5), 5.52 (m, H at C3 and C4), 3.02 (d, J=5.4 Hz, H at C2), 3.67 (s, OCH$_3$); methyl octadec-cis-3-enoate: δ 2.02 (m, H at C5), 5.52 (m, H at C3 and C4), 3.08 (d, J=5.1 Hz, H at C2), 3.67 (s, OCH$_3$). The $^1$H NMR spectrum of the starting methyl oleate in CDCl$_3$ follows: δ 5.32 (m, 2 H, olefin H), 1.99 (m, 4 H, CH$_2$ at C8 and C11), 1.60 (m, 2 H, CH$_2$ at C3), 2.28 (t, J=7.5 Hz, 2 H, CH$_2$ at C2), 3.64 (s, 3 H, OCH$_3$), 0.86 (t, J=6.6 Hz, 3 H, CH$_3$ at C18), 1.25–1.28 (m, 20 H, remaining CH$_2$ groups).

Reaction of CO with an Irradiated Solution of Fe(CO)$_5$ and Ethyl 4-Methyl-4-Pentenoate. A hexanes solution (20 mL) of Fe(CO)$_5$ (35 μL, 0.27 mmol) and ethyl 4-methyl-4-pentenoate (43 μL, 0.27 mmol) was irradiated at 0° C. for 3 hours with a continuous N$_2$ flow to produce Fe(CO)$_3$($\eta^4$-Pr$^i$CH=CHCO$_2$Et). The solution was then purged with CO at 0° C. for 1 hour, followed by stirring under CO at 50° C. overnight. Volatile compounds including Fe(CO)$_5$ produced during the reaction, free ethyl 4-methyl-4-pentenoate and its isomers, and hexanes were transferred to another vessel by bulb-to-bulb vacuum distillation. The Fe(CO)$_5$ and hexanes in this transferred solution were then removed by distillation at 0° C. under vacuum (0.1 mm Hg) leaving a mixture of esters, which were analyzed by GC and GC-MS. These compounds were identified by the following $^1$H NMR spectra in CDCl$_3$ which are very similar to those reported in the literature (Frost et al., *Chem. Phys. Lipids*, 15, 53, 1975): ethyl-4-methyl-4-pentenoate: δ 4.65 (s, olefin H at C5), 4.70 (s, olefin H at C5), 1.70 (s, CH$_3$ at C4), 2.40 (t, J=7.8 Hz, CH$_2$ at C3), 2.29 (t, J=7.8 Hz, CH$_2$ at C2), 4.09 (q, J=7.2 Hz, OCH$_2$CH$_3$), 1.21 (t, J=7.2 Hz, OCH$_2$CH$_3$); ethyl 4-methyl-3-pentenoate: δ 1.74 (s, CH$_3$ at C4), 1.63 (s, CH$_3$ at C4), 5.31 (t, J=6.9 Hz, olefin H at C3), 3.02 (d, J=6.9 Hz, CH$_2$ at C2), 4.09 (q, J=7.2 Hz, OCH$_2$CH$_3$), 1.21 (t, J=7.2 Hz, OCH$_2$CH$_3$); ethyl 4-methyl-trans-2-pentenoate: δ 1.06 (d, J=6.6 Hz, CH$_3$ at C4), 2.45 (m, H at C4), 6.94 (d of d, J=15.6 and 6.6 Hz, olefin H at C3), 5.76 (d, J=15.6 Hz, olefin H at C2); ethyl 4-methyl-cis-2-entenoate: δ 1.06 (d, J=6.6 Hz, CH$_3$ at C4), 2.34 (m, H at C4), 6.00 (d of d, J=11.4 and 9.2 Hz, olefin H at C3), 5.65 (d, J=11.4 Hz, olefin H at C2).

Thermal Reaction of Fe(CO)$_3$($\eta^2$-cis-cyclooctene)$_2$ with Methyl Oleate. Cis-cyclooctene (2.7 mmol) and Fe(CO)$_5$ (0.27 mmol) in hexanes (20 mL) were irradiated at −35° C. while a continuous N$_2$ flow was maintained over the surface of the solution in order to remove liberated CO. Irradiation was continued (2 hours) until Fe(CO)$_5$ and the intermediate Fe(CO)$_4$($\eta^2$-cis-cyclooctene) had largely disappeared, and Fe(CO)$_3$($\eta^2$-cis-cyclooctene)$_2$ was the only major product, as established by FTIR spectroscopy (Fleckner et al., *J. Am. Chem. Soc.*, 106, 2027, 1984). See Table 1, below. Then, methyl oleate (2.7 mmol) was added to the solution, followed by warming to 0° C. This solution was stirred at 0° C. for 3 hours, during which time samples were removed periodically for FTIR and GC analysis.

Thermal Reaction of Fe$_2$(CO)$_9$ with Methyl Oleate. To a Schlenk tube containing Fe$_2$(CO)$_9$ (97 mg, 0.27 mmol) suspended in toluene (20 mL) was added methyl oleate (0.27 mmol). The mixture was stirred at 50° C. Periodically the solution was analyzed by GC for the organic compounds and by FTIR spectroscopy for the iron carbonyl compounds.

Synthesis and Isolation of Methyl Octadec-trans-2-enoate. A hexanes solution (20 mL) of methyl oleate (0.27 mmol) and pentacarbonyl iron (0.27 mmol) in a quartz flask was irradiated for three hours at 0° C. using a 450 W mercury ultraviolet lamp while the solution was stirred and purged with nitrogen in order to remove liberated carbon monoxide. The solvent was removed under reduced pressure to produce tricarbonyl($\eta^4$-methyl octadec-trans-2-enoate) iron and a mixture of tetracarbonyl($\eta^2$-methyl octadecenoate)iron internal isomers in yields of 70% and 30%, respectively. The residue was treated with an ethanol solution (20 mL) of cerium(IV) ammonium nitrate (CAN, 10 mmol) at room temperature for one hour to give a bright orange solution containing a mixture of the unsaturated fatty acid methyl esters (FAMEs). The solvent was removed under reduced pressure and the solid residue was dissolved in 20 mL of water; this solution was extracted with n-pentane (3×20 mL). The organic layer was evaporated, the semisolid product was purified by flash chromatography on silica gel using hexanes/methylene chloride (3:1). The semisolid product was dissolved in a minimal amount of hot methanol. The mixture was cooled to 0° C. and white crystals formed, which were collected by filtration, and washed with cold methanol. The recrystallization was repeated twice. The resultant α,β-unsaturated isomer, methyl octadec-trans-2-enoate, was isolated using double recrystallization from methanol in a 13–18% yield of 94% pure product (by $^1$H NMR).

The electron withdrawing ester group in this compound makes the C=C bond more reactive to Michael type nucleophilic addition and [4+2] cycloaddition reactions.

Methyl octadec-trans-2-enoate undergoes nucleophilic addition of various amines, such as piperidine, to afford the β-aminoester derivative. This reaction can also be accomplished with the FAMEs mixture as follows. A mixture of methyl octadec-trans-2-enoate (or the mixture of FAMEs) (0.5 mmol) and neat piperidine (1.0 mmol) was heated in an oil bath at 50° C. for 10 hours. The excess of piperidine was removed under reduced pressure to yield a dark yellow residue. This residue was dissolved in hexanes (5 mL) and extracted with 18% solution of hydrochloric acid (5 mL). The acid layer was separated, treated with sodium hydroxide (25% aqueous solution) to give pH 7, and extracted with hexanes (4×10 mL). The solvent was removed under reduced pressure to afford methyl 3-(1-piperidino) octadecanoate in 26–30% yield.

Methyl octadec-trans-2-enoate also reacts with 2,3-dimethylbutadiene at elevated temperatures to give the methyl 3,4-dimethyl-6-pentadecylcyclohex-2-enecarboxylate. Although this cycloaddition reaction can be carried out with FAMEs, the product was not isolable when the mixture of FAMEs was used. This reaction was carried out as follows. A mixture of methyl octadec-traits-2-enoate (or the mixture of FAMEs) (0.1 mmol) and neat 2,3- dimethylbutadiene (0.5 mmol) was heated in a sealed tube at 150° C. for 10 hours. The excess of 2,3-dimethylbutadiene was removed under reduced pressure. The residue was purified by flash chromatography using silica gel and hexanes/methylene chloride (1:1) in a 71% yield.

Results

Figure 1A:
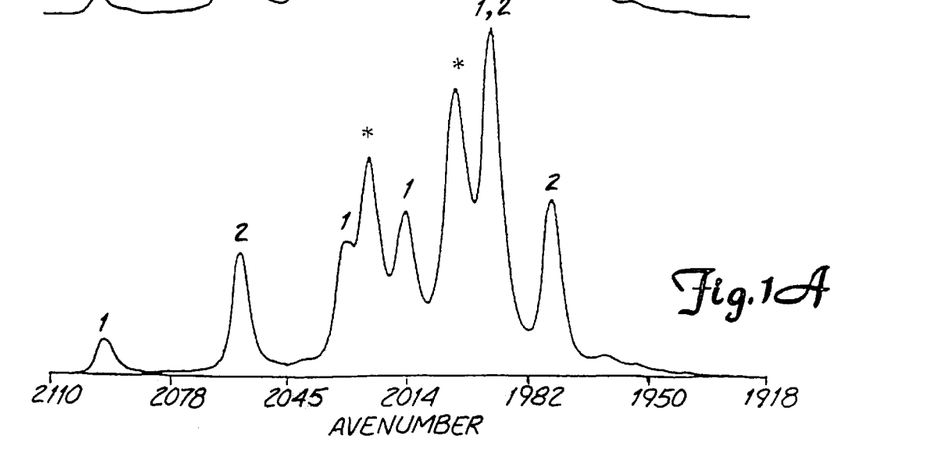
FIG. 1a. FTIR Spectrum of the UV-irradiated solution of CH$_3$CH=CHCO$_2$Me (13.3 mM) and Fe(CO)$_5$ (13.3 mM) in hexanes at 0° C. after 0.5 hour irradiation. 1=Fe(CO)$_4$($\eta^2$-methyl crotonate); 2=Fe(CO)$_3$($\eta^4$-methyl crotonate); *=Fe(CO)$_5$.

Irradiation of Fe(CO)$_5$ and Methyl trans-Crotonate in Hexanes. When a hexanes solution of Fe(CO)$_5$ (13 mM) and methyl trans-crotonate (13 mM) at 0° C. is irradiated with UV light, the FTIR spectrum (FIG. 1a) of the solution after 0.5 hour of irradiation shows a decrease in the intensities of the Fe(CO)$_5$ bands (see Table 1, below) at 2023 cm$^{-1}$ and 2000 cm$^{-1}$ due to the reaction of Fe(CO)$_5$. FIG. 1a also shows the appearance of several new bands indicating the formation of Fe(CO)$_4$($\eta^2$-CH$_3$CH=CHCO$_2$Me) (1) and Fe(CO)$_3$($\eta^4$-CH$_3$CH=CHCO$_2$Me) (2). The bands at 2059 (m), 1991 (s), and 1976 (s) cm$^{-1}$ are assigned to the v(CO) absorptions of Fe(CO)$_3$($\eta^4$-CH$_3$CH=CHCO$_2$Me) (2) by comparing them with v(CO) bands of the known complex Fe(CO)$_3$($\eta^4$-CH$_2$=CHCO$_2$Me) at 2064 (m), 1994 (s), and 1979 (s) cm$^{-1}$ (see Table 1, below). The absorptions at 2096 (m), 2029 (s), 2014 (s) and 1991 (s) cm$^{-1}$ are assigned to the v(CO) bands of Fe(CO)$_4$($\eta^2$-CH=CH=CHCO$_2$Me) (1) following the previous assignments for this compound. The decrease in intensity of the 1735 cm$^{-1}$ v(C=O) band for free methyl trans-crotonate after 0.5 hour of irradiation indicates that approximately 28% of the methyl trans-crotonate has reacted. Compound 2 also exhibits a band at 1504 cm$^{-1}$ which is assigned to v(C=C) of the $\eta^4$-coordinated CH$_3$CH=CHCO$_2$CH$_3$ in 2 based on the analogous band in Fe(PF$_3$)$_3$($\eta^4$-CH$_3$CH=CHCO$_2$CH$_3$) as shown in Kruck et al., Chem. Ber., 106, 3578, 1973. A new band at 1717 cm$^{-1}$ is assigned to v(C=O) of the $\eta^2$-coordinated methyl trans-crotonate in 1; this assignment is based on the v(C=O) value (1710 cm$^{-1}$) of the coordinated CH$_2$=CHCO$_2$Me in Fe(PF$_3$)$_4$($\eta^2$-CH$_2$=CHCO$_2$Me) disclosed in Koerner von Gustorf et al., Z. Naturforschg., 27b, 575, 1972 and Kruck et al., Chem. Ber., 106, 3578, 1973.

Figure 1B:
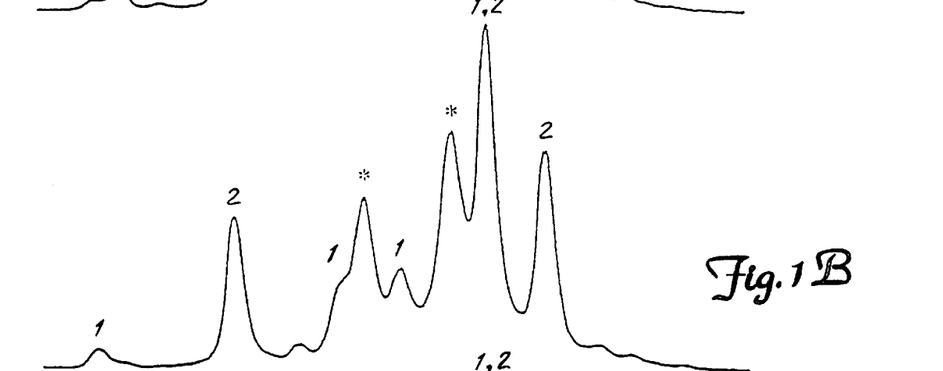
FIG. 1b. FTIR Spectrum of the UV-irradiated solution of CH$_3$CH=CHCO$_2$Me (13.3 mM) and Fe(CO)$_5$ (13.3 mM) in hexanes at 0° C. after 1 hour irradiation. 1=Fe(CO)$_4$($\eta^2$-methyl crotonate); 2=Fe(CO)$_3$($\eta^4$-methyl crotonate); *=Fe(CO)$_5$.
Figure 1C:
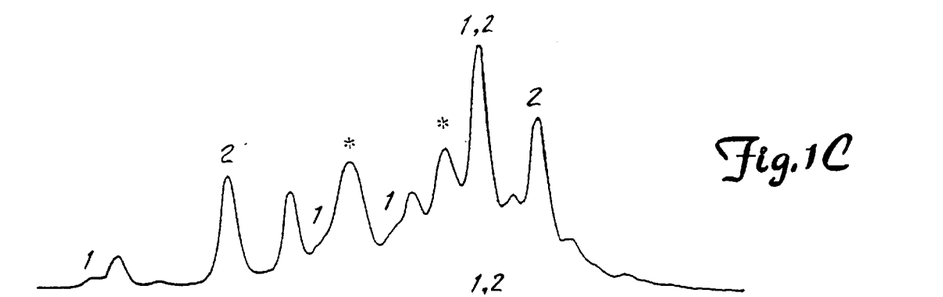
FIG. 1c. FTIR Spectrum of the UV-irradiated solution of CH$_3$CH=CHCO$_2$Me (13.3 mM) and Fe(CO)$_5$ (13.3 mM) in hexanes at 0° C. after 5 hours irradiation. 1=Fe(CO)$_4$($\eta^2$-methyl crotonate); 2=Fe(CO)$_3$($\eta^4$-methyl crotonate); *=Fe(CO)$_5$.

After 1 hour of irradiation, the FTIR spectrum (FIG. 1b) of the solution shows that the concentration of 2 increases while the concentration of 1 decreases, and about 24% of the free methyl crotonate is left in solution. Upon further irradiation (5 hours) (FIG. 1c), the concentrations of both 1 and 2 decrease, but free methyl crotonate increases (30%). A few bands in the spectra (FIG. 1) could not be assigned to specific compounds. After the 5 hour-irradiated solution was armed to room temperature for one hour, the concentration of 2 decreased significantly while the concentrations of 1 and Fe(CO)$_5$ increased. Irradiated hexanes solutions of Fe(CO)$_5$ and the other olefin-esters discussed herein exhibit FTIR spectra that are very similar to those in FIG. 1.

Irradiation of Fe(CO)$_5$ and Methyl 3-Butenoate in Hexanes. In order to study olefin isomerization under the same conditions used in the formation of 2 from Fe(CO)$_5$ and methyl trans-crotonate (Equation 2), a hexanes solution of Fe(CO)$_5$ (13.3 mM) and methyl 3-butenoate (13.3 mM) was irradiated at 0° C. (Equation 3).

The v(CO) bands (see Table 1, below) in the FTIR spectrum of the solution after 0.5 hour of irradiation indicate that complexes 1* and 2 are formed. The intermediate Fe(CO)$_4$($\eta^2$-olefin ester) (1*) is likely to be a mixture of 1, as indicated by the v(C=O) band at 1717 cm$^{-1}$ and v(CO) band at 2096 cm$^{-1}$, and Fe(CO)$_4$($\eta^2$-CH$_2$=CHCH$_2$CO$_2$Me), as indicated by the band at 2087 cm$^{-1}$. During the initial 0.5 hour of irradiation, the decrease in intensity of the v(C=O) band for free methyl 3-butenoate at 1752 cm$^{-1}$ indicates that 33% of the methyl 3-butenoate remains uncoordinated. Free methyl trai7s-crotonate is also produced, as shown by a band at 1735 cm$^{-1}$. This establishes that the C=C double bond in methyl 3-butenoate isomerizes to the α,β-position during the irradiation in the presence of Fe(CO)$_5$. Upon longer irradiation, the concentration of 1 decreases while the concentration of 2 increases. The highest concentration of 2 was obtained after 1.5 hours; it then decreased with further irradiation (6 hours). The concentration of the free methyl 3-butenoate decreases throughout the irradiation also; only 12% of the free methyl 3-butenoate remains after 1.5 hours, but its concentration does not increase upon prolonged irradiation (6 hours). However, the concentration of free methyl trans-crotonate does increase during longer irradiation (6 hours). When after 6 hours of irradiation, the solution was treated with CO to liberate the methyl crotonate from 2, the reaction mixture consisted of 94% methyl trans-crotonate and 6% of the starting methyl 3-butenoate. When methyl 3-butenoate, in the absence of Fe(CO)$_5$, is irradiated under the same conditions (hexanes solvent, 0° C., 6 hours), no methyl trans-crotonate is produced. It might be noted that UV-photolysis (5 hours) of methyl trans-crotonate in hexanes at 0° C. gave 27% methyl cis-crotonate, 4% methyl 3-butenoate and 69% unreacted methyl trans-crotonate; UV-promoted isomerization of methyl trans-crotonate has been previously reported by Kropp et al., J. Org. Chem., 32, 3222, 1967.

Irradiation of Fe(CO)$_5$ and Ethyl 4-Methyl-4-Pentenoate in Hexanes. When the branched-chain olefin-ester, ethyl 4-methyl-4-pentenoate (13.3 mM), is irradiated for 0.5 hour with Fe(CO)$_5$ (13.3 mM) in hexanes at 0° C., an FTIR spectrum shows that Fe(CO)$_3$($\eta^4$-Pr$^i$CH=CHCO$_2$Et) (3) is formed (Equation 4) as indicated by the v(CO) peaks at 2058, 1990, and 1973 cm$^{-1}$.

There are also bands for Fe(CO)$_4$($\eta^2$-olefin-ester) complexes. Upon treatment with excess pyridine, the bands for 3 completely disappear, and a strong v(C=O) band at 1731 cm$^{-1}$ for the free α,β-ester trans-Pr$^i$CH=CHCO$_2$Et is observed; the formation of the α,β-ester was confirmed by a GC-MS analysis of the reaction solution (Lauwers et al., Org. Mass Spect., 7, 1027, 1973; and Bowles et al., Org. Mass Spect., 2, 809, 1969). The concentration of 3 increases initially, then decreases after longer irradiation times, as detected in FTIR spectra of the solution. The FTIR spectra show that the highest concentration of 3 is obtained after 3 hours of irradiation; GC analysis of the pyridine-treated solution also shows that the highest yield of trans-Pr$^i$CH=CHCO$_2$Et (90%) is obtained after 3 hours of irradiation. The yield decreases to 69% after 6 hours of irradiation. When the reaction was conducted at 20° C. (see Table 2, entries 14,15, below), the maximum yield (83%) was lower than at 0° C. and was achieved in 1 hour.

Reaction of CO with an Irradiated Solution of Fe(CO)$_5$ and Ethyl 4-Methyl-4-Pentenoate. In order to release ethyl 4-methyl-2-pentenoate from 3 produced during the irradiation (Equation 4) and to recycle the starting Fe(CO)$_5$, the hexanes solution of Fe(CO)$_5$ (13.3 mM) with ethyl 4-methyl-4-pentenoate (13.3 mM) that had been irradiated for 3 hours at 0° C. was purged with CO at 0° C. (Equation 5).

An FTIR spectrum of the solution after 1 hour of reaction with CO showed that 3 disappeared completely, and the concentration of the Fe(CO)$_4$($\eta^2$-$\alpha,\beta$-ester) complex 4 increased significantly. Further purging (2 hours) of the solution with CO at 0° C. did not convert 4 to Fe(CO)$_5$. However, after the CO-saturated solution had been stirred at 50° C. for 12 hours, the FTIR spectrum of the solution then showed that 4 had completely disappeared. The major Fe product in the solution was Fe(CO)$_5$; its concentration was approximately 12.5 mM, which is slightly less than the 13.3 mM used in the initial reaction (Equation 4). A GC analysis of the solution showed that 90% of the product was the $\alpha,\beta$-ester, ethyl 4-methyl-trans-2-pentenoate; the other isomers were present in small amounts. A $^1$H NMR spectrum of the ester mixture showed that more than 99% of the $\alpha,\beta$-ester is the trans isomer as indicated by the characteristic chemical shifts and coupling constants of the C3 and C2 olefinic protons at δ 6.94 (J=15.6 and 6.6 Hz) and 5.76 (J=15.5 Hz).

Irradiation of Fe(CO)$_5$ with Methyl Oleate in Hexanes. A hexanes solution of Fe(CO)$_5$ (13.3 mM) and the long chain olefin-ester methyl oleate (13.3 mM) was irradiated at 0° C. (Equation 6).

An FTIR spectrum of the solution after 0.5 hour of irradiation showed that Fe(CO)$_3$($\eta^4$-CH$_3$(CH$_2$)$_{14}$CH=CHCO$_2$Me) (6) was the major product as indicated by bands at 2058, 1990, and 1975 cm$^{-1}$. A mixture of Fe(CO)$_4$($\eta^2$-olefin-ester) intermediates 5 were also observed; a ν(CO) band at 2077 cm$^{-1}$ suggests that most of these compounds contain the non-$\alpha,\beta$-unsaturated isomers, while the weak band at 2094 cm$^{-1}$ indicates the presence of some of the $\eta^2$-$\alpha,\beta$-unsaturated ester complex 8. Complex 6 is stable at 0° C. for at least 1 hour as FTIR spectra of the stirred solution in the dark for 1 hour show no significant change. However, significant decomposition of 6 occurs when the solution is stirred at room temperature for 1 hour, as the concentrations of Fe(CO)$_5$ and 5 increase. If the solution (Equation 6) obtained from 0.5 hour of irradiation at 0° C. is stirred with 20-fold pyridine (py) for 10 minutes, all of 6 disappears and new bands at 2051, 1968, 1942, and 1863 cm$^{-1}$ are observed, indicating the formation (van Dijk et al., *J. Organomet. Chem.*, 340, 227, 1988; and Schubert et al., *Inorg. Chem.*, 5, 1071, 1966) of Fe(CO)$_3$(py)$_2$ and Fe(CO)$_4$(py) (Equation 7).

The band at 1717 cm$^{-1}$ for ν(C=O) of the ester group in 5 disappears completely. And the intensity of the band at 1735 cm$^{-1}$ for ν(C=O) of the free $\alpha,\beta$-ester, methyl octadec-trans-2-enoate (7), increases significantly.

The identity of 7 formed in reaction (7) was confimed by GC-MS studies. GC analysis of the reaction solution showed five peaks at retention times ranging from 9 minutes to 11 minutes. The peak at 10.5 minutes showed lines in the mass spectrum at e/m 87 and 113 for methyl acrylate and an oxacyclohexadiene, respectively, which are characteristic fragments observed in mass spectra of $\alpha,\beta$-unsaturated methyl esters (Lauwers et al., *Org. Mass Spect.*, 7, 1027, 1973; and Bowles et al., *Org. Mass Spect.*, 2, 809, 1969). Other GC fractions showed mass spectra characteristic of other isomers of methyl oleate in which the olefin is not in the $\alpha,\beta$-position. These non-$\alpha,\beta$-ester isomers in the four remaining GC peaks were not assigned to specific isomers. Quantitative GC analysis of the mixture showed that >97% of the original methyl oleate was recovered from reactions (6) and (7) as methyl oleate or its isomers; for this determination a known amount of methyl palmitate CH$_3$(CH$_2$)$_{14}$CO$_2$CH$_3$ was added to the reaction solution as the internal standard.

The reaction (Equation 6) of Fe(CO)$_5$ (13.3 mM) and methyl oleate (13.3 mM) in hexanes at 0° C. was monitored by FTIR spectroscopy for the production of the iron carbonyl complexes and examined by GC for the yield of 7 by treating samples from the reaction solutions with excess pyridine (Equation 7) at times ranging from 0.5 hour to 7 hours from the beginning of the reaction. FTIR spectra of the solutions showed that the concentration of 6 increases during the first three hours of irradiation but then decreases upon further irradiation (7 hours). The ν(C=O) absorbance at 1749 cm$^{-1}$ for methyl oleate and its non-$\alpha,\beta$-ester isomers decreases during the first three hours and then increases at longer irradiation times. Yields of the $\alpha,\beta$-ester obtained from GC analyses parallel those obtained by FTIR using the ν(C=O) band of the free methyl oleate and Fe(CO)$_4$($\eta^2$-non-$\alpha,\beta$-ester) at 1749 cm$^{-1}$; the intensity of this band decreases as methyl oleate is converted to 6. The yields of the $\alpha,\beta$-ester 7 increase from 45% after 0.5 hour of irradiation to 70% after 3 hours of irradiation, and then drop to 60% after 7 hours (see Table 2, entries 1–3, below). When a solution of methyl oleate (13.3 mM) in hexanes was irradiated for 6 hour without Fe(CO)$_5$, the α,β-ester 7 was not detected.

When technical grade methyl oleate (containing 76% methyl oleate as determined by GC) and Fe(CO)$_5$ were irradiated under the same conditions (13.3 mM, hexanes solvent, 0° C., followed by pyridine displacement), the maximum yield (67%, based on the initial methyl oleate) of the α,β-ester 7 was achieved after 3 hours. The yields after 2 hours and 4 hours were 62% and 61%, respectively.

Besides pyridine (Equation 7), CO was also used to liberate the α,β-ester 7 from its iron complex 6 produced during the irradiation; this treatment also regenerates the starting Fe(CO)$_5$ (Equation 8).

A hexanes solution of Fe(CO)$_5$ (13.3 mM) and methyl oleate (13.3 mM) that had been irradiated for 3 hours at 0° C. was purged with CO at 0° C. An FTIR spectrum of the solution, after reaction with CO for 1 hour, showed that 6 disappeared completely while the concentration of Fe(CO)$_4$(η$^2$-α,β-ester) (8) increased significantly. Further purging of the solution with CO for 2 hours at 0° C. did not convert 8 to Fe(CO)$_5$; nor did stirring the CO-saturated solution at room temperature for 12 hours. However, stirring the CO-saturated solution at 50° C. for 12 hours resulted in the complete disappearance of Fe(CO)$_4$(η$^2$-α,β-ester) (8) as indicated by the FTIR spectrum. The major iron product in the solution was Fe(CO)$_5$, and its concentration as determined by the intensity of its 2023 cm$^{-1}$ band was approximately 12.5 mM, which is 94% of the initial Fe(CO)$_5$ used in the reaction shown in Equation 6. GC analysis of the solution showed that more than 99% of the initial methyl oleate was recovered as its isomeric esters (primarily 7). A $^1$H NMR spectrum of the ester mixture demonstrated that more than 98% of the α,β-ester 7 was the trans isomer; this assignment is based on the chemical shifts and characteristically large coupling constants of the trans olefinic protons at δ 6.96 (J=15.5 and 7.2 Hz) and 5.81 (J=15.5 and 1.5 Hz).

Concentration Effects. When a hexanes solution of relatively high concentration Fe(CO)$_5$ (40 mM) and methyl oleate (40 mM) was irradiated according to Equation 6 at 0° C., yellow Fe$_2$(CO)$_9$ precipitated from solution. Its FTIR spectrum (nujol mull) contained ν(CO) bands at 2081 (s), 2017 (vs), 1985 (sh), and 1826 (s) cm$^{-1}$ that are identical to those obtained of a known sample of Fe$_2$(CO)$_9$ (Griffith et al., *J. Chem. Soc.* (A), 834. 1969; and Kristoff et al., *Inorg. Chem.*, 13, 499, 1974). The yield of 7 obtained by GC analysis of the solution treated with excess pyridine increases during irradiation and reaches its highest value of 42% after 5 hours (see Table 2, entry 6, below); this is less than the 70% yield of the α, β-ester (7) obtained from the reaction at lower concentrations (13.3 mM) of Fe(CO)$_5$ and methyl oleate.

Solvent Effect. In an attempt to improve the yield of the α,β-ester and inhibit the formation of Fe$_2$(CO)$_9$ at the higher reactant concentrations, toluene and THF solutions of Fe(CO)$_5$ (40 mM) and methyl oleate (40 mM) were irradiated at 0° C. (see Table 2, entries 7, 8, below). In the experiment using toluene as the solvent, much yellow Fe$_2$(CO)$_9$ precipitated, and the highest yield (38%) of the α,β-ester was obtained after 5 hours of irradiation; this yield is slightly smaller than that (42%) obtained in hexanes solvent. In the experiment using THF as the solvent, there was no yellow precipitate, but the FTIR spectrum of the irradiated solution showed no bands indicating the formation of 8 or 6. The only new band occurred at 2075 cm$^{-1}$ which may be assigned (Table 1) to Fe(CO)$_4$(L) (L=non-α,β-ester isomers of methyl oleate or THF). GC analysis of the solution showed that the methyl oleate isomerized, but the yield of the α,β-ester (5% after 5 hours) was very low. It increased throughout the irradiation until it reached a maximum at 5% after 5 hours. Further irradiation of the solution (17 hours) did not change the yield of the α,β-ester but isomerization of the methyl oleate and its non-α,β-ester isomers continued as determined by GC. In another experiment, no solvent was used. Equal volumes of Fe(CO)$_5$ (0.25 mL) and methyl oleate (0.25 mL) were mixed and then irradiated. Much precipitation of Fe$_2$(CO)$_9$ occurred and the maximum yield of the α,β-ester was about 5%. Based on these studies, hexanes solvent gave the highest yield of the α,β-ester.

Irradiation of Fe(CO)$_5$ with Methyl Oleate in the Presence of THF or cis-Cyclooctene. In an attempt to improve the yield of the α,β-ester and prevent the formation of Fe$_2$(CO)$_9$ at relatively high reactant concentrations, the weakly coordinating ligands THF (80 mM) or cis-cyclooctene (40 mM) were added to the hexanes solution of Fe(CO)$_5$ (40 mM) and methyl oleate (40 mM) for irradiation at 0° C. (see Table 2, entries 9, 10, below). Added THF (80 mM) gave a maximum yield (36%) of the α,β-ester which is lower than that (42%) obtained in the absence of THF. With cis-cyclooctene (40 mM), the maximum yield was only 30%. In both experiments, a yellow precipitate of Fe$_2$(CO)$_9$ was observed.

Temperature Effect. The temperature of the reaction also had an important effect on the yield (see Table 2, entries 4,5, below). During the irradiation of 13.3 mM Fe(CO)$_5$ and methyl oleate in hexanes at 20° C., the highest yield (58%) of the α,β-ester (7) was obtained after 1 hour; this is a lower yield than that (70%) obtained after 3 hours of irradiation at 0° C. Prolonged irradiation (4 hours) reduces the yield of the α,β-ester to 49%. Stirring the solution (after 4 hours of irradiation) in the dark at 20° C. for 1 hour lowers the concentration of 6 by 60% as determined by FTIR, and the final yield of the α,β-ester (7) is only 42%.

In an experiment at 20° C. using higher concentrations (40 mM) of Fe(CO)$_5$ and methyl oleate, only a small amount of Fe$_2$(CO)$_9$ recipitate was observed during irradiation. However, the highest yield (47%) of 7, obtained after 1.5 hour of irradiation, was only slightly larger than that obtained at 0° C. (42%). When another portion of Fe(CO)$_5$ (40 mM) was added to the solution after 1.5 hour of irradiation, much Fe$_2$(CO)$_9$ precipitated during further irradiation (1 hour), but the yield of 7 did not improve.

Irradiation of Methyl Oleate with a Catalytic Amount of Fe(CO)$_5$. A hexanes solution of Fe(CO)$_5$ (13.3 mM) with 10 equivalents of methyl oleate (133 mM) was irradiated at 0° C. The yield (based on the amount of methyl oleate) of 7 determined by GC increased during the initial 5.5 hours to a maximum of 13%. Additional irradiation (21 hours) did not change the yield. The 13% yield is similar to that expected for 70% conversion of one equivalent of methyl oleate to 7 and 4–5% conversion of 9 equivalents to a thermodynamic yield of 7.

Thermal Isomerization of Methyl Oleate Promoted by Fe(CO)$_3$(cis-cyclooctene)$_2$. Fe(CO)$_3$(cis-cyclooctene)$_2$ was synthesized in situ by irradiating a hexanes solution of Fe(CO)$_5$ (13.3 mM) and 20 equivalents of cis-cyclooctene (266 mM) at −35° C. (Equation 9).

$$\text{Fe(CO)}_5 + \text{C}_8\text{H}_{14} \text{ (excess)} \xrightarrow[-35°\text{C.}]{\text{hv}} \text{Fe(CO)}_3(\text{C}_8\text{H}_{14})_2 \xrightarrow[0°\text{C.}]{\text{methyl oleate}} 6 \quad (9)$$

$\text{C}_8\text{H}_{14} = \text{cis-cyclooctene}$

After the addition of methyl oleate (133 mM), the solution was warmed to 0° C. during which time the color of the solution gradually turned from pale yellow to red. The FTIR spectrum of the solution after stirring at 0° C. for 0.5 hour showed that most of the Fe(CO)$_3$(cis-cyclooctene)$_2$ had reacted with methyl oleate to give 6 and several unidentified complexes with v(CO) bands ranging from 2100 cm$^{-1}$ to 1900 cm$^{-1}$. Some Fe(CO)$_5$ is also produced. GC analysis of a sample of the solution pre-treated with excess pyridine gave a 30% yield of the α,β-ester (7) based on the amount of Fe(CO)$_5$ used. Further stirring of the solution for 4 hours did not improve the yield of the α,β-ester, although isomerization of methyl oleate into the other non-α,β-ester isomers continued to proceed as shown from the GC data.

In a similar experiment, Fe(CO)$_3$(cis-cyclooctene)$_2$ was synthesized by irradiation of Fe(CO)$_5$ (13.3 mM) with a lesser amount of cis-cyclooctene (53 mM). When this solution was reacted in the dark at 0° C. with methyl oleate (13.3 mM), the highest yield of the α,β-ester was 18% based on the amount of Fe(CO)$_5$ used.

Thermal Reaction of Methyl Oleate and Fe$_2$(CO)$_9$. A toluene solution of methyl oleate (13.3 mM) was stirred at 50° C. with Fe$_2$(CO)$_9$ (13.3 mM) suspended in the solution. After 2 hours of stirring, only 1% of the α,β-ester was observed from a GC analysis of the solution. Prolonged stirring (12 hours) at 50° C. does not increase the yield of the α,β-ester, but methyl oleate is isomerized to its non-α,β-ester isomers as determined by GC. When the same mixture was allowed to react at 0° C., only a very low yield (1%) of 7 was obtained.

A similar reaction using 133 mM methyl oleate and 13.3 mM Fe$_2$(CO)$_9$ in toluene at 50° C. gave a similar yield of the α,β-ester (2.5%). A reaction of Fe$_2$(CO)$_9$ (13.3 mM) and methyl oleate (133 mM) carried out in THF at 50° C. also gave a very small yield (<5%) of the α,β-ester.

In other attempts to generate Fe(CO)$_3$(η$^4$-α,β-ester) (6) by non-photolytic methods, equimolar (13.3 mM) methyl oleate and Fe(CO)$_5$ were reacted with excess (40 mM) Me$_3$NO (Shen et al., *Coord. Chem. Rev.*, 128, 69, 1993) at 0° C. in toluene solvent. After 1 hour, most of the Fe(CO)$_5$ had reacted; Fe(CO)$_4$(NMe$_3$) was the major product based on the strong band at 2047 cm$^{-1}$; Fe(CO)$_4$(η$^2$-methyl oleate) was the minor product based on the band at 2074 cm$^{-1}$. There was no change in their concentrations during 24 hours, but warming to 20° C. resulted in slow decomposition of both species. There was no evidence for 6, and GC analysis of the mixture, after pyridine treatment, showed that the α,β-ester (7) was not formed. When an even higher concentration of Me$_3$NO (133 mM) or another amine oxide, N-methylmorpholine N-oxide (40 mM), was used, neither 6 nor 7 was formed. When iodosobenzene, PhIO (Shen et al., *Coord. Chem. Rev.*, 128, 69, 1993), was used as the decarbonylating agent (26.6 mM in CH$_2$Cl$_2$ at 0° C.) in the reaction of Fe(CO)$_5$ with methyl oleate, the Fe(CO)$_5$ slowly disappeared but no new iron carbonyl complexes were formed. Thus, the oxide decarbonylating agents were unsuccessful for converting methyl oleate to its α,β-ester (7).

Thermodynamic Amount of α,β-Ester (7) from Isomerization of Methyl Oleate. Using a procedure similar to that reported (Singer et al., *Tetrahedront*, 28, 5769, 1972) for the isomerization of other olefin-esters, the equilibrium amount of 7 generated by isomerization of methyl oleate was determined by using RhCl(PPh$_3$)$_3$ (12 mg, 1.3×10$^{-5}$ mol) and SnCl$_2$.2H$_2$O (5.3×10$^{-5}$ mol) as the catalyst system for the isomerization of methyl oleate (88 μL, 2.6×10$^{-4}$ mol) in chlorobenzene (4 mL) at 115° C. The GC traces showed 6 peaks for various isomers of methyl oleate but only the α,β-ester (7) was identified. After 2 days, there was no change in the amount (3.5%) of 7. To further confirm that equilibrium had been achieved, another portion of methyl oleate (88 μL, 2.6×10$^{-4}$ mol) was added to the reaction mixture. After 3 days, the equilibrium amount of 7 was again 3.5% of the reacting methyl oleate.

TABLE 1

IR Data for Relevant Compounds

| Compounds | v(CO) in hexanes (cm$^{-1}$) |
|---|---|
| CH$_2$=CHCH$_2$CO$_2$Me | 1752 (m) |
| CH$_3$(CH$_2$)$_7$CH=CH(CH$_2$)$_7$CO$_2$Me | 1749 (m) |
| CH$_2$=C(CH$_3$)(CH$_2$)$_2$CO$_2$Et | 1745 (m) |
| trans-CH$_3$CH=CHCO$_2$Me | 1735 (m) |
| CH$_3$(CH$_2$)$_{14}$CH=CHCO$_2$Me (7) | 1735 (m) |
| trans-Pr$^i$CH=CHCO$_2$Et | 1731 (m) |
| Fe(CO)$_5$ | 2023 (s), 2000 (s) |
| Fe(CO)$_4$(η$^2$-CH$_3$CH=CHCO$_2$Me) (1) | 2096 (m), 2029 (s), 2014 (s), 1991 (s), 1717 (m)$^a$ |
| Fe(CO)$_4$(η$^2$-CH$_3$(CH$_2$)$_{14}$CH=CHCO$_2$Me (8) | 2094 (m), 2032 (s), 2014 (s), 1990 (s), 1717 (m)$^a$ |
| Fe(CO)$_4$(η$^2$-Pr$^i$CH=CHCO$_2$Et) (4) | 2095 (m), 2031 (s), 2014 (s), 1990 (s), 1713 (m)$^a$ |
| Fe(CO)$_4$(pyridine) | 2051 (m), 1968 (s), 1942 (s) |
| Fe(CO)$_4$(η$^2$-cis-cyclooctene)$^b$ | 2077 (m), 2000 (s), 1994 (s), 1973 (s) |
| Fe(CO)$_4$(η$^2$-methyl oleate) | 2077 (m), 2036 (s), 1992 (s), 1973 (s) |
| Fe(PF$_3$)$_4$(η$^2$-CH$_2$=CHCO$_2$Me)$^c$ | 1710 (m) |
| Fe(CO)$_3$(η$^4$-CH$_2$=CHCO$_2$Me)$^d$ | 2064 (m), 1994 (s), 1979 (s) |
| Fe(CO)$_3$(η$^4$-CH$_3$CH=CHCO$_2$Me) (2) | 2059 (m), 1991 (s), 1976 (s) |
| Fe(CO)$_3$(η$^4$-CH$_3$(CH$_2$)$_{14}$CH=CHCO$_2$Me) (6) | 2058 (m), 1990 (s), 1975 (s) |
| Fe(CO)$_3$(η$^4$-Pr$^i$CH=CHCO$_2$Et) (3) | 2058 (m), 1990 (s), 1973 (s) |
| Fe(CO)$_3$pyridine$_2$ | 1863 (s) |
| Fe(CO)$_3$(η$^2$-cis-cyclooctene)$_2$$^b$ | 2043 (m), 1965 (s) |
| Fe(PF$_3$)$_3$(η$^4$-CH$_3$CH=CHCO$_2$Me)$^c$ | 1379 (m) |

$^a$v(C=O) of η$^2$-coordinated olefin-ester.
$^b$See Fleckner et al., J. Am. Chem. Soc., 106, 2027, 1984.
$^c$See Kruck et al., Chem. Ber., 106, 3578, 1973.
$^d$See Grevels et al., Angew. Chem. Int. Ed. Engl., 13, 534, 1974.

TABLE 2

Yields of α,β-Esters Obtained from UV-Promoted Isomerizations of Olefin-Esters in the Presence of Fe(CO)$_5$

| Entry | Olefin-Esters | Conc$^a$ mM | Temp °C. | solvent | time | α,β-ester yield$^d$ |
|---|---|---|---|---|---|---|
| 1 | methyl oleate | 13.3 | 0 | hexanes | 0.5 h | 45% |
| 2 | methyl oleate | 13.3 | 0 | hexanes | 3 h | 70% |
| 3 | methyl oleate | 13.3 | 0 | hexanes | 7 h | 60% |
| 4 | methyl oleate | 13.3 | 20 | hexanes | 1 h | 58% |
| 5 | methyl oleate | 13.3 | 20 | hexanes | 4 h | 49% |
| 6 | methyl oleate | 40 | 0 | hexanes | 5 h | 42% |
| 7 | methyl oleate | 40 | 0 | toluene | 5 h | 38% |
| 8 | methyl oleate | 40 | 0 | THF | 5 h | 5% |
| 9 | methyl oleate | 40 | 0 | hexanes$^b$ | 5 h | 36% |
| 10 | methyl oleate | 40 | 0 | hexanes$^c$ | 5 h | 30% |
| 11 | methyl oleate | 40 | 20 | hexanes | 1.5 h | 47% |
| 12 | 4-ethyl-4-pentenoate | 13.3 | 0 | hexanes | 3 h | 90% |

TABLE 2-continued

Yields of α,β-Esters Obtained from UV-Promoted
Isomerizations of Olefin-Esters in the Presence of Fe(CO)$_5$

| Entry | Olefin-Esters | Conc[a] mM | Temp °C. | solvent | time | α,β-ester yield[d] |
|---|---|---|---|---|---|---|
| 13 | 4-ethyl-4-pentenoate | 13.3 | 0 | hexanes | 6 h | 69% |
| 14 | 4-ethyl-4-pentenoate | 13.3 | 20 | hexanes | 1 h | 83% |
| 15 | 4-ethyl-4-pentenoate | 13.3 | 20 | hexanes | 2 h | 78% |

[a]Equal concentrations of Fe(CO)$_5$ and the olefin-ester were used.
[b]THF (80 mM) is present in the solution.
[c]cis-cyclooctene (40 mM) is present in the solution.
[d]Determined by pyridine displacement method.

The complete disclosure of all patents, patent documents, and publications cited herein are incorporated by reference. The foregoing detailed description and example have been given for clarity of understanding only. No unnecessary limitations are to be understood therefrom. The invention is not limited to the exact details shown and described, for variations obvious to one skilled in the art will be included within the invention defined by the claims.

What is claimed is:

1. A process for the synthesis of an α,β-unsaturated ester, the process comprising:
   (a) exposing a mixture of a mono-olefin-ester and Fe(CO)$_5$ to ultraviolet radiation; and
   (b) adding a coordinating ligand or oxidizing agent to the mixture under conditions effective to produce an α,β-unsaturated ester.

2. The process of claim 1 wherein the exposing step is carried out under conditions effective to form the α,β-unsaturated ester in a yield of at least about 25%.

3. The process of claim 2 wherein the exposing step is carried out under conditions effective to form the α,β-unsaturated ester in a yield of at least about 70%.

4. The process of claim 1 wherein the exposing step is carried out at a temperature no greater than about 20° C.

5. The process of claim 4 wherein the exposing step is carried out at a temperature of no greater than about 0° C.

6. The process of claim 1 wherein the exposing step comprises exposing approximately equimolar amounts of the Fe(CO)$_5$ and the mono-olefin-ester to ultraviolet radiation.

7. The process of claim 6 wherein the Fe(CO)$_5$ and the mono-olefin-ester are initially present in the mixture at concentrations of no greater than about 500 mM.

8. The process of claim 7 wherein the Fe(CO)$_5$ and the mono-olefin-ester are initially present in the mixture at concentrations of no greater than about 15 mM.

9. The process of claim 1 wherein the coordinating ligand is selected from the group of pyridine, CO, a phosphine, an arsine, an amine, a sulfide, and a diene olefin.

10. The process of claim 1 wherein the mixture of the mono-olefin-ester and Fe(CO)$_5$ further includes a noncoordinating solvent.

11. The process of claim 1 wherein the mono-olefin ester is of the formula (R$^1$)(R$^2$)C=C(R$^3$)—R$^4$—CO$_2$R$^5$ wherein each R$^1$, R$^2$, and R$^3$ are independently H or an alkyl group, R$^4$ is a divalent alkylene group, and R$^5$ is an alkyl group.

12. A process for the synthesis of an α,β-unsaturated ester, the process comprising:
   (a) combining a mono-olefin-ester and Fe(CO)$_5$ under conditions effective to form Fe(CO)$_3$(η$^4$-α,β-ester); and
   (b) adding a displacing reagent to the Fe(CO)$_3$(72$^4$-α,β-ester) to displace the α,β-ester ligand and form free α,β-unsaturated ester.

13. The process of claim 12 wherein the process is carried out under conditions effective to form the α,β-unsaturated ester in a yield of at least about 25%.

14. The process of claim 12 wherein the combining step is carried out in the presence of ultraviolet radiation at a temperature of no greater than about 0° C.

15. The process of claim 12 wherein the displacing reagent comprises a coordinating ligand or an oxidizing agent.

16. The process of claim 15 wherein the coordinating ligand is selected from the group of pyridine, CO, a phosphine, an arsine, an amine, a sulfide, and a diene olefin.

17. The process of claim 12 wherein the mono-olefin ester is of the formula (R$^1$)(R$^2$)C=C(R$^3$)—R$^4$—CO$_2$R$^5$ wherein each R$^1$, R2, and R3 are independently H or an alkyl group, R$^4$ is a divalent alkylene group, and R$^5$ is an alkyl group.

18. A process for the synthesis of an α,β-unsaturated ester, the process comprising:
   (a) exposing Fe(CO)$_5$ to ultraviolet radiation in the presence of a weakly coordinating ligand to form Fe(CO)$_3$L$_x$, wherein L represents the weakly coordinating ligand and x=1 or 2;
   (b) adding a mono-olefin-ester to the Fe(CO)$_3$L$_x$ to form Fe(CO)$_3$(η$^4$-α,β-ester); and
   (c) adding a displacing reagent to the Fe(CO)$_3$(η$^4$-α,β-ester) to displace the α,β-ester ligand and form free α,β-unsaturated ester.

19. The process of claim 18 wherein the weakly coordinating ligand L is selected from the group of an alkene, an ether, an alkyl or aryl halide, and an ester.

20. The process of claim 18 wherein the displacing reagent comprises a coordinating ligand or an oxidizing agent; wherein the coordinating ligand is selected from the group of pyridine, CO, a phosphine, an arsine, an amine, a sulfide, and a diene olefin, and the oxidizing agent is O$_2$.

21. A process for the synthesis of an ester, the process comprising:
   (a) combining a mono-olefin-ester and Fe(CO)$_5$ under conditions effective to form Fe(CO)$_3$(η$^4$-α,β-ester); and
   (b) treating Fe(CO)$_3$(η$^4$-α,β-ester) with an electrophile to form an ester.

22. The process of claim 21 wherein the electrophile comprises an acid of the form HX, wherein X is F, Cl, Br, I, CH$_3$CO$_2$, RSO$_3$, R$_3$PO$_4$, and the like.

* * * * *